United States Patent [19]

Haas et al.

[11] Patent Number: 5,831,121

[45] Date of Patent: Nov. 3, 1998

[54] PROCESS FOR THE PRODUCTION OF 3-HYDROXY PROPIONIC ACID OR A SALT THEREOF

[75] Inventors: Thomas Haas, Frankfurt; Martin Meier, Werl; Christoph Brossmer, Frankfurt; Dietrich Arntz, Oberursel; Andreas Freund, Kleinostheim, all of Germany

[73] Assignee: Degussa Aktiengesellschaft, Hanau, Germany

[21] Appl. No.: 897,529

[22] Filed: Jul. 21, 1997

[30] Foreign Application Priority Data

Jul. 20, 1996 [DE] Germany ............... 196 29 371.5

[51] Int. Cl.$^6$ ................................. C07C 51/235
[52] U.S. Cl. ........................................... 562/531
[58] Field of Search ............................... 562/531

[56] References Cited

U.S. PATENT DOCUMENTS 3,483,249 12/1969 Platz .......................... 260/530

FOREIGN PATENT DOCUMENTS

WO 92/16489 10/1992 WIPO .

*Primary Examiner*—Gary Geist
*Assistant Examiner*—Rosalynd Keys
*Attorney, Agent, or Firm*—Wenderoth, Lind & Ponack

[57] ABSTRACT

3-hydroxy propionic acid is obtained in high yield through the catalytic oxidation of 3-hydroxy propionaldehyde with $O_2$ or an $O_2$-containing gas in the aqueous phase in the presence of a platinum-group catalyst, in particular a Pd or Pt supported catalyst. The catalyst is used in a quantity corresponding to at least 10 percent by weight of the platinum-group metal relative to 3-hydroxy propionaldehyde.

14 Claims, No Drawings

PROCESS FOR THE PRODUCTION OF 3-HYDROXY PROPIONIC ACID OR A SALT THEREOF

The invention is directed toward a process for the production of 3-hydroxy propionic acid or a salt thereof, and is based on the catalytic oxidation of a $C_3$ starting material with oxygen or an oxygen-containing gas in the presence of an precious metal catalyst. According to the invention 3-hydroxy propionaldehyde is used as the $C_3$ starting material.

BACKGROUND OF THE INVENTION

3-Hydroxy propionic acid as well as its water-soluble salts are valuable synthesis starting materials. 3-Hydroxy propionic acid is conventionally produced by the hydration of acrylic acid or by the conversion of ethylene chlorohydrin with sodium cyanide (Ullman's Encyclopedia of Industrial Chemistry, 5th Edition, Volume A-13, Pages 507 to 517). In the case of the hydration of acrylic acid, the reaction is an equilibrium reaction, i.e. the conversions are limited. In the case of the conversion of ethylene chlorohydrin, the use of highly toxic substances is required and, in addition, a hydrolysis stage must follow. This leads to a high salt accumulation of sodium chloride and ammonium salts. According to DE-A 41 07 986 these disadvantages can be avoided by oxidizing 1,3-propanediol with oxygen or an oxygen-containing gas to 3-hydroxy propionic acid in the presence of a supported catalyst comprising palladium. As demonstrated by the examples, 3-hydroxy propionic acid is obtained in a yield up to approximately 82%. According to JP-A 56/5433, through the catalytic oxidation of 1,3-propanediol in the presence of 3.3 percent by weight of palladium relative to the diol, 3-hydroxy propionic acid can be obtained at a yield of 84%. But this document does not teach carrying out the oxidation only up to the stage of the 3-hydroxy propionic acid.

According to EP-B 0 350 741, glucose, thus a hydroxyaldehyde, can be oxidized in the presence of a Pd or Pt catalyst to form gluconic acid. As has been found, with the quantities of catalyst specified in this document of less than 2 percent by weight of the precious metal, relative to glucose, 3-hydroxy propionaldehyde cannot be oxidized to 3-hydroxy propionic acid with a higher yield.

DESCRIPTION OF THE INVENTION

The object of the present invention resides in a further process for the production of 3-hydroxy propionic acid or a salt thereof through the catalytic oxidation of a $C_3$ starting material leading to a high yield. The process should preferably be carried out such that 3-hydroxy propionic acid can be isolated from a salt-free reaction mixture.

Accordingly, a process for the production of 3-hydroxy propionic acid or a salt thereof was found comprising the catalytic oxidation of a $C_3$ starting material with oxygen or an oxygen-containing gas in the presence of a catalyst containing a precious metal from the platinum group in the aqueous phase, and isolation of the 3-hydroxy propionic acid or a salt thereof from the reaction mixture, which is characterized in that as the $C_3$ starting material 3-hydroxy propionaldehyde is used and the catalyst is used in a quantity corresponding to at least 10 percent by weight of the precious metal relative to the $C_3$ starting material.

Specific preferred embodiments of the process according to the invention are disclosed.

The $C_3$ starting material in the process according to the invention is 3-hydroxy propionaldehyde. This starting material is more readily accessible than the 1,3-propanediol previously used, and can be obtained enzymatically from glycerol or through hydration of acrolein with the subsequent hydrogenation of the hydroxy propionaldehyde (see for example EP-B 0 412 337). By using 3-hydroxy propionaldehyde as the $C_3$ starting material in the process according to the invention, one oxidation equivalent less is accordingly required than for the oxidation of 1,3-propanediol.

The catalytic oxidation is catalyzed by a precious metal from the platinum group, such as Ru, Rh, Pd, Os, Ir and Pt. Preferred catalysts comprise palladium or platinum. These can be pure metal catalysts or supported catalysts. Supported catalysts comprising palladium and platinum are preferred. As the supporting material, particularly suitable are activated charcoal as well as oxidic and silicatic materials.

One characteristic feature according to the invention is the quantity of the catalyst to be used in the catalytic oxidation. It was found that by increasing the quantity of the catalyst—the reference quantity herein is the quantity of precious metal—the yield increases sharply and thus 3-hydroxy propionic acid can be obtained in nearly quantitative yield. The catalyst is conveniently used in a quantity corresponding to at least 10 percent by weight of the precious metal relative to the $C_3$ starting material. Preferred is a quantity of at least 20 percent by weight of the precious metal relative to the $C_3$ starting material.

The catalytic oxidation can be carried out using a suspension catalyst in a suspension reactor as well as using a fixed-bed catalyst in a fixed-bed reactor. If the catalyst, preferably a supported catalyst, is disposed in a fixed-bed reactor, the latter can be operated in a trickle-bed procedure as well as also in a liquid-phase procedure. In the trickle-bed procedure the aqueous phase comprising the $C_3$ starting material, as well as the oxidation products of the same and means for adjusting the pH, and oxygen or an oxygen-containing gas can be conducted in parallel flow or counterflow. In the liquid-phase procedure the liquid phase and the gas phase are conveniently conducted in parallel flow. While in the trickle-bed procedure a sufficiently large interfacial area exists automatically between the liquid phase and the gas phase, in the case of the liquid-phase procedure as well as with the oxidation in a suspension reactor, care must be taken that a good dispersion of the oxygen or the oxygen-containing gas in the liquid phase is obtained.

Since, according to the invention the catalyst should be used in the largest possible quantity relative to the $C_3$ starting material, oxidation using a fixed-bed reactor is especially advantageous. In this embodiment the required ratio of weight is achieved quasi-automatically. The reaction mixture can be conducted one time or several times over the fixed-bed reactor so that the pH-value can be adjusted outside of the reactor.

The $C_3$ starting material is supplied to the oxidation reaction in the aqueous phase. The concentration of the $C_3$ starting material in the aqueous phase is conveniently in the range between 1 and 30 percent by weight, preferably between 1 and 10 percent by weight. 3-Hydroxy propionaldehyde as the $C_3$ starting material can be used in the form of an aqueous solution with a content between approximately 5 and 20 percent by weight, such as is readily obtained by the acid-catalyzed hydration of acrolein with the subsequent separation of the nonconverted acrolein, either directly or after dilution, with water.

In order to attain, in particular when using a palladium catalyst, a sufficiently short reaction time, the conversion is carried out at a pH-value of equal to or greater than 6, preferably at least 7, and in particular between 7.5 and 9. According to a preferred embodiment, during the oxidation reaction the pH-value is kept constant, preferably at a pH-value in the range between 7.5 and 9, by adding a base. As the base, there is preferably used a 10 to 50 percent by weight aqueous alkali metal or alkaline earth metal hydroxide solution.

According to an especially preferred embodiment a platinum catalyst, in particular a supported catalyst containing a platinum, is used. Herein, surprisingly, regulation of the pH-value is not necessary. Consequently, the oxidation takes place in the acid phase and 3-hydroxy propionic acid can be isolated directly from the reaction mixture. The process thus proceeds salt-free whereby technical expenditures can be reduced.

The oxidation is usefully carried out at a temperature of at least 10° C. and maximally 70° C. A preferred temperature range is between 20° and 60° C., in particular between 40° and 60° C. At a temperature above 70° C., 3-hydroxy propionaldehyde is not very stable and, in addition, discoloration occurs.

The throughflow of oxygen is not limited. In the case of the suspension procedure it is important to bring the liquid and the gaseous phase into contact through vigorous stirring. The conversion is not very pressure-dependent so that it is carried out usefully at autogenous or slightly increased pressure, for example up to 3 bars.

From the aqueous reaction mixture obtained from the oxidation reaction carried out at a pH-value of greater than 6, in particular greater than 7, comprising 3-hydroxy propionic acid-salt, 3-hydroxy propionic acid can be obtained in a manner known per se, for example by conversion with sulfuric acid and extraction of the 3-hydroxy propionic acid or by treatment of the reaction solution with an acidic ion exchanger.

As is clearly evident in the following examples and comparison examples, by using the quantity of catalyst as claimed, it is possible to obtain 3-hydroxy propionic acid in very high yields. According to a preferred embodiment the processing of a salt-containing reaction mixture can be omitted.

EXAMPLES

All of the following examples and comparison example were carried out in a 1 l mixing flask. In each case, an aqueous 3-hydroxy propionaldehyde (HPA) solution was used. The solution was exposed to oxygen introduced at 30 l/h via a glass frit. The reaction temperature was 50° C. To the extent adjustments of the pH-value were carried out, sodium hydroxide was used for this purpose. As the catalyst in the examples and the comparison examples, 3% and 5%, respectively, Pd/activated charcoal (E 105 XR/W 3% and 5%, respectively, Degussa AG) as well as 5% Pt/activated charcoal (F 105 R/W 5%, Degussa AG) was used.

The product composition was analyzed by means of HPLC. For the separation, two amino columns SEPIL by Jasco connected in series were used. As the elution agent a mixture of acetonitrile and 0.03 molar $KH_2PO_4$ at a ratio of 6 to 4 was used. The column temperature was 35° C., the flow rate was 1 ml/min.

Comparison Example 1

5 g of 5% Pd/activated charcoal catalyst, 90 g 10% HPA solution and 400 g of water were mixed and exposed in a 1 l mixing flask to oxygen introduced at 30 l/h. The reaction temperature was 50° C. During the reaction enough sodium hydroxide was introduced for the pH-value to remain at pH=8. After a reaction time of 2.5 hrs the product composition was analyzed by means of HPLC. An HPA conversion of 83.5% and a hydroxy propionic acid selectivity of 66%, corresponding to a yield of 55.1%, was attained.

Comparison Example 2

5 g of 5% Pt/activated charcoal catalyst, 90 g of 10% HPA solution and 400 g of water were mixed and exposed in a 1 l mixing flask to oxygen introduced at a rate of 30 l/h. The reaction temperature was 50° C. Regulation of the pH-value during the reaction was not carried out. After a reaction time of 8.5 h, the product composition was analyzed by means of HPLC. An HPA conversion of 4.8% and a hydroxy propionic acid selectivity of 99.5% was achieved, corresponding to a yield of 4.8%.

Example 1

100 g of 3% Pd/activated charcoal catalyst, 90 g 10% HPA solution and 500 g water were mixed and exposed in a 1 l mixing flask to oxygen introduced at 30 l/h. The reaction temperature was 50° C. During the reaction enough sodium hydroxide was added for the pH-value to remain constant at pH=8. After 1 h of reaction time the product composition was analyzed by means of HPLC. An HPA conversion of 87.9% and a hydroxy propionic acid selectivity of 89.5%, corresponding to a yield of 78.7%, was attained.

Comparison of Example 1 with Comparison Example 1 shows that only through a high fraction of catalyst in the reactor can a satisfactory hydroxy propionic acid selectivity and thus also a high yield be achieved. In addition, through this measure the reaction time is markedly shortened. It follows from the Comparison Examples 1 and 2 that, when using a palladium catalyst, the regulation of the pH-value becomes necessary since otherwise no sufficient conversion can be achieved.

Comparison Example 3

5.5 g of 5% Pt/activated charcoal catalyst, 90 g 10% HPA solution and 400 g water were mixed and exposed in a 1 l mixing flask to oxygen introduced at a rate of 30 l/h. The reaction temperature was 50° C. A regulation of the pH during the reaction was omitted. After a reaction time of 4 hours the product composition was analyzed by means of HPLC. An HPA conversion of 14.6% and a hydroxy propionic acid selectivity of 98.5%, corresponding to a yield of 14.4%, was achieved.

Example 2

50 g of 5% Pt/activated charcoal catalyst, 90 g of 10% HPA solution and 450 g water were mixed and exposed in a 1 l mixing flask to oxygen introduced at 30 l/h. The reaction temperature was 50° C. Regulation of the pH during the reaction was omitted. After a reaction time of 2.5 h the product composition was analyzed by means of HPLC. An HPA conversion of 87.4% and a hydroxy propionic acid selectivity of 93.6%, corresponding to a yield of 84.4%, was attained.

Example 3

50 g of 5% Pt/activated charcoal catalyst, 90 g of 10% HPA solution and 450 g water were mixed and exposed in a 1 l mixing flask to oxygen introduced at the rate of 30 l/h. The reaction temperature was 50° C. A regulation of the pH during the reaction was omitted. After a reaction time of 4 h the product composition was analyzed by means of HPLC. An HPA conversion of 97.2% and a hydroxy propionic acid selectivity of 95.6%, corresponding to a yield of 92.9%, was attained.

Examples 2 and 3 show that when using a Pt catalyst, regulation of the pH is not required.

What is claimed is:

1. In a process for the production of 3-hydroxy propionic acid or a salt thereof, comprising the catalytic oxidation of a $C_3$ starting material with oxygen or an oxygen-containing gas in the presence of a catalyst comprising a precious metal from the platinum group in the aqueous phase and isolation of the 3-hydroxy propionic acid or a salt thereof from the reaction mixture, the improvement wherein as the $C_3$ starting material 3-hydroxy propionaldehyde is used and the catalyst is used in a quantity corresponding to at least 10 percent by weight of the precious metal relative to the $C_3$ starting material.

2. A process as claimed in claim 1, wherein the catalyst is used in a quantity corresponding to 20 to 50 percent by weight relative to the $C_3$ starting material.

3. A process as claimed in claim 1, wherein as the catalyst a supported catalyst comprising palladium or platinum is used.

4. A process as claimed in claim 2, wherein as the catalyst a supported catalyst comprising palladium or platinum is used.

5. A process as claimed in claim 3, wherein the catalyst is disposed in a fixed-bed reactor and the latter is operated
(i) in a trickle-bed procedure, wherein the aqueous phase and oxygen or an oxygen-containing gas are conducted in parallel flow or counterflow, or
(ii) in a liquid-phase procedure with the liquid phase and the gas being conducted in parallel flow.

6. A process as claimed in claim 4, wherein the catalyst is disposed in a fixed-bed reactor and the latter is operated
(i) in a trickle-bed procedure, wherein the aqueous phase and oxygen or an oxygen-containing gas are conducted in parallel flow or counterflow, or
(ii) in a liquid-phase procedure with the liquid phase and the gas being conducted in parallel flow.

7. A process as claimed in claim 1, wherein the oxidation is carried out using a palladium-containing catalyst at a pH-value of at least 6.

8. A process according to claim 7 wherein the pH value is between 7.0 and 9.

9. A process as claimed in claim 2, wherein the oxidation is carried out using a palladium-containing catalyst at a pH-value of at least 6.

10. A process according to claim 9 wherein the pH value is between 7.0 and 9.

11. A process as claimed in claim 1, wherein the oxidation is carried out at a temperature in the range of 20° to 60° C.

12. A process as claimed in claim 2, wherein the oxidation is carried out at a temperature in the range of 20° to 60° C.

13. A process as claimed in claim 1, wherein the catalytic oxidation is carried out using a supported catalyst comprising platinum with the regulation of the pH.

14. A process as claimed in claim 2, wherein the catalytic oxidation is carried out using a supported catalyst comprising platinum with the regulation of the pH.

* * * * *